(12) United States Patent
Allmendinger et al.

(10) Patent No.: US 6,329,552 B2
(45) Date of Patent: Dec. 11, 2001

(54) BENFLUMETOL DERIVATIVES, INTERMEDIATES THEREOF AND THEIR USE AGAINST PARASITICAL PROTOZOA AND TREMATODES

(75) Inventors: Thomas Allmendinger, Lörrach; Walther Helmut Wernsdorfer, Vienna, both of (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/746,041

(22) Filed: Dec. 22, 2000

Related U.S. Application Data

(63) Continuation of application No. PCT/EP99/04355, filed on Jun. 23, 1999.

(30) Foreign Application Priority Data

Jun. 25, 1998 (CH) .................................................. 1351/98

(51) Int. Cl.⁷ .................................................. A61K 31/135
(52) U.S. Cl. .......................................... 564/338; 514/650
(58) Field of Search ............................. 564/338; 514/650

(56) References Cited

FOREIGN PATENT DOCUMENTS

WO 92/02217    2/1992    (WO) .

OTHER PUBLICATIONS

International Search Report.
Deng Rong–Xian, "Recent Progress in Research on antimalarials in China", Chinese Journal of Pharmaceuticals, vol. 20, No. 8, (1989).
World Health Organization Technical Report Series 805, Report of WHO Scientific Group, "Practical chemotherapy of malaria", pp. 124–126 (1990).
Deng, Rong–Xian et al., Chemical Abstractd, vol. 114 p. 6046 (1991), CN 1,042,535, May 30, 1990.
Chemical Abstracts 101: 136941u, Wang Yunling et al., , "Stability of antimalarial fluorenemethanol in soft capsules", Yaowu Fenxi Zazhi, vol. 4, No. 2, pp. 84–87 (1984).
Chemical Abstracts 97:28538h, Wang Yunling et al., "Enhancement of bioavailability of a hydrophobic fluorenemethanol antimalarial by oleic acid in soft gelatin capsules", Yaoxue Tongbao, vol. 17, No. 1, 4–7, (1982).
Deng, Rogxian et al., Chemical Abstracts XP002119016, "Studies on antimalarial agents", p. 575, col. 1 (1982).

*Primary Examiner*—Samuel Barts
(74) *Attorney, Agent, or Firm*—Susan Hess

(57) ABSTRACT

The invention relates to a compound of formula (I),

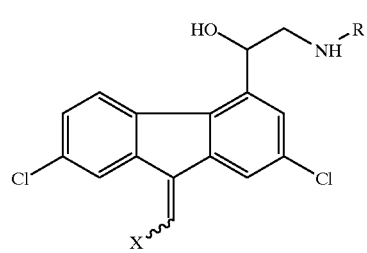

wherein R is an alkyl unsubstituted by one or more polar substituents or an alkenyl unsubstituted or substituted by one or more polar substituents, and X is aryl, or salts thereof. The compounds are effective e.g. against protozoa and trematodes.

19 Claims, No Drawings

BENFLUMETOL DERIVATIVES, INTERMEDIATES THEREOF AND THEIR USE AGAINST PARASITICAL PROTOZOA AND TREMATODES

This is a continuation of International Application No. PCT/EP99/04355, filed Jun. 23, 1999, the contents of which are incorporated herein by reference.

SUMMARY OF THE INVENTION

The invention relates to N-substituted 2-amino-1-[2,7-dichloro-9-(aryl)-9H-fluoren-4-yl]-ethanols, methods for the preparation of these compounds, new intermediate products, pharmaceutical preparations and fixed or variable combinations comprising these compounds, the use of these compounds (alone or in fixed or free combination) and/or combinations for the therapeutic or prophylactic treatment of diseases or for the preparation of pharmaceutical preparations and methods for the therapeutic or prophylactic treatment of warm-blooded animals comprising the administration of these compounds or combinations.

BACKGROUND TO THE INVENTION

Parasitic diseases, in particular those caused by protozoa (such as malaria, pathogens: plasmodia), or by trematodes (such as schistosomiasis, for example urinary schistosomiasis, caused by schistosomes, as Schistosoma haematobium), constitute a substantial proportion of the diseases, especially in developing countries. Malaria, transmitted by the Anopheles mosquito and caused by protozoa of the Plasmodium genus, is a disease which occurs in about 100 million people each year, of whom around one million die. A distinction is drawn between *Malaria tropica* (caused by *Plasmodium falciparum*), *Malaria tertiana* (caused by *Plasmodium vivax* or *Plasmodium ovale*) and *Malaria quartana* (caused by *Plasmodium malariae*). *Malaria tropica* is the most severe form of the disease.

Benflumetol (also lumefantrine), a compound of formula

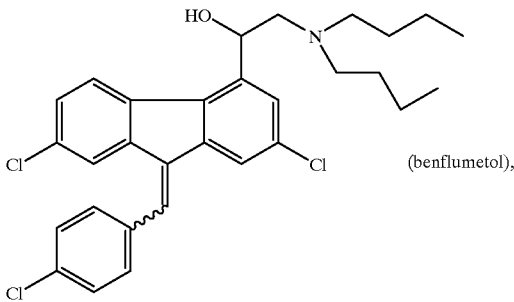

(benflumetol), is a compound which, in combination with artemether (see EP 0 500 823)—a sesquiterpene lactone derivative of the naturally occurring substance artemisinin with the name [3R-(3α, 5αβ, 6β, 8αβ, 9α, 10α, 12β,-12 aR)]-decahydro-10-methoxy-3,6,9-trimethyl-3,12epoxy-12H-pyrano[4,3j]-1,2-benzodioxepin, is in the review stage for approval worldwide as a treatment for malaria.

Because of phenomena such as the development of resistance, it remains an urgent necessity to find new compounds which show particularly good efficacy against malaria and minimal toxicity.

The different half-lives of the substances which are active against malaria also mean that further compounds should be made available which show a pharmacokinetic behaviour distinct from the antimalarial substances already established. Chloroquine, for example, has a very long half-life, artemether a relatively short half-life (2 hours in plasma), and benflumetol for example has a plasma half-life of 4–6 days in patients.

The solubility of benflumetol is also not very good, and when it is taken for example with foods having a high fat content the absorption can be up to 16 times higher than it is in the absence of such fatty foods, so that dosing cannot be optimally controlled.

Surprisingly, a new class of compounds has now been found which have a number of beneficial properties, meet one or more of the above requirements in particular, and facilitate for example the treatment of severe cases of malaria or a corresponding prophylaxis, or in the broader sense of schistosomiasis, the prevention or treatment of potentially multiresistant malaria, and new pharmaceutical formulations, and thus an improved pharmacokinetics, but in particular show especially good efficacy against plasmodia.

DETAILED DESCRIPTION OF THE INVENTION

The invention relates to a compound of formula I,

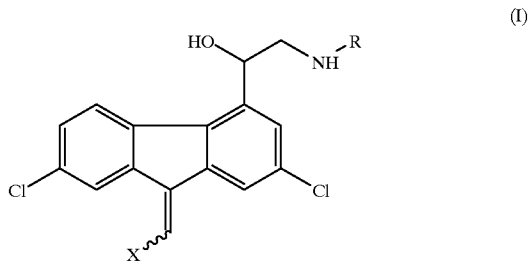

(I)

wherein R is an alkyl unsubstituted or substituted by one or more polar substituents or an alkenyl unsubstituted or substituted by one or more polar substituents, and X is aryl, or a salt thereof.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Any asymmetric carbon atoms may be present in the (R)—, (S)— or (R,S) configuration, preferably in the (R)— or (S) configuration. Substituents at a double bond or a ring may be present in cis- (=Z—) or trans (=E—) form. The compounds may thus be present as mixtures of isomers or as pure isomers, preferably as enantiomer-pure diastereomers. Especially preferred are in each case the E or Z form of a compound of formula 1, which with regard to the C—OH in formula I are present as an enantiomeric mixture (in particular a racemate). The enantiomer-pure E and Z forms are also important.

Alkyl may be a singly or multiply branched or straight-chain substituent; alkyl preferably has up to 10 carbon atoms and especially up to 8 carbon atoms, and is in particular $C_1$–$C_5$alkyl, for example n-pentyl, n-butyl, sec-butyl, tert-butyl, n-propyl, isopropyl, ethyl or methyl, or octyl, for example n-octyl. Methyl, n-pentyl, n-butyl and sec-butyl are especially preferred.

Alkyl with up to 8 carbon atoms which is substituted by a polar radical, preferably n-pentyl, n-butyl or sec-butyl, is especially substituted by one or more, especially up to three polar substituents selected from the group consisting of amino, N-lower alkylamino, N,N-di-lower alkylamino, hydroxy, hydroxy-lower alkoxy, such as 2-hydroxyethoxy, hydroxy-lower alkoxy-lower alkoxy, such as 2-(2-hydroxyethoxy)ethoxy, carboxy, amidino and guanidino, especially amino, hydroxy and guanidino. If otherwise unstable compounds are present, such substituents are preferably not bonded on the carbon-1 atom (which bonds R to the nitrogen in formula 1).

Alkenyl is preferably alkenyl with up to 8 carbon atoms and is in particular lower alkenyl with 3 to 7, especially 3 or 4 carbon atoms, wherein the carbon atom binding the nitrogen in formula I may not form a double bond (double bond only in the 2 position or higher, because otherwise the compound would be unstable).

Alkenyl which is substituted by a polar radical and has up to 8 carbon atoms, in particular $C_3$–$C_7$lower alkenyl, is substituted especially by one or more, in particular up to three polar substituents selected from the group consisting of amino, N-lower alkylamino, N,N-di-lower alkylamino, hydroxy, carboxy, amidino and guanidino, especially amino, hydroxy and guanidino. In the case of hydroxy, amino, lower alkylamino and guanidino, this substituent may not be bonded to a carbon atom which is linked to the radical of the molecule via a double bond. If otherwise unstable compounds are present, such substituents are moreover preferably not bonded on the carbon-1 atom (the atom which bonds R to the nitrogen in formula 1) (this is often the case especially with hydroxy, amino, and guanidino).

Halogen is above all fluorine, chlorine, bromine, or iodine, especially fluorine, chlorine, or bromine.

Aryl is in particular $C_6$ to $C_{14}$aryl, especially fluorenyl, napthyl or in particular phenyl, the said radicals being unsubstituted or substituted by one or more substituents selected from the group comprising halogen, especially chlorine; hydroxy; substituted hydroxy, in particular lower alkanoyloxy, phenyl-lower alkoxy or lower alkoxy; amino; monosubstituted or disubstituted amino, in particular amino substituted by lower alkanoyl, phenyl-lower alkyl or lower alkyl monosubstituted or disubstituted amino; lower alkyl; substituted lower alkyl, such as phenyl-lower alkyl, halogen-lower alkyl, cyano-lower alkyl, carbamoyl-lower alkyl, carboxy-lower alkyl, lower alkoxycarbonyl-lower alkyl or phenyl-lower alkoxycarbonyl-lower alkyl substituted lower alkyl; phenyl; naphthyl; carboxy; esterified carboxy, for example lower alkoxycarbonyl, phenyl-lower alkoxycarbonyl or phenoxycarbonyl, amidino, cyano, nitro and sulfo. Aryl is in particular 4-chlorophenyl.

Salts are primarily the pharmaceutically acceptable salts of compounds of formula I.

Such salts are formed, for example, as acid addition salts, preferably with organic or inorganic acids, from compounds of formula I with a basic nitrogen atom. Suitable inorganic acids are, for example, halogen acids, such as hydrochloric acid; sulfuric acid; or phosphoric acid. Suitable organic acids are for example carboxylic, phosphonic, sulfonic or sulfamic acids, for example acetic acid, glycolic acid, lactic acid, fumaric acid, succinic acid, adipic acid, malic acid, tartaric acid, citric acid, glucaric acid, galactaric acid, amino acids, such as glutamic acid, aspartic acid, maleic acid, hydroxymaleic acid, benzoic acid, phenylacetic acid, methane- or ethanesulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, N-cyclohexylsulfamic acid, N-methyl, N-ethyl, or N-propyl-sulfamic acid, or other organic protonic acids, such as ascorbic acid.

In the presence of negatively charged radicals, such as carboxy, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

In the presence of a basic group and an acid group in the same molecule, a compound of formula 1 may also form internal salts.

For isolation or purification purposes it is also possible to use pharmaceutically unacceptable salts, for example picrates or perchlorates. Only the pharmaceutically acceptable salts or free compounds (if the occasion arises, in the form of pharmaceutical preparations) attain therapeutic use, and these are therefore preferred.

In view of the close relationship between the novel compounds in free form and in the form of their salts, including those salts that can be used as intermediates, for example in the purification or identification of the novel compounds, any reference hereinbefore and hereinafter to the free compounds is to be understood as referring also to the corresponding salts, as appropriate and expedient.

Compounds of formula I show beneficial pharmacological properties. In particular they show a high degree of efficacy against protozoa, such as plasmodia, and also against trematodes, such as schistosomes.

The efficacy against plasmodia, in particular against *Plasmodium falciparum*, can be determined according to methods known per se, for example according to the method described in Example 6.

Inhibitory constants of the following order of magnitude are shown for compounds of formula I:

$EC_{50}$ (concentration showing half the maximum inhibitory efficacy versus controls not given active substance): 1 to 200, preferably 1 to 20 nmol/l.

$EC_{99}$ (concentration showing half the maximum inhibitory efficacy versus controls not given active substance): 10 to 1000, preferably 10 to 110 nmol/l.

This in vitro model of *Plasmodium falciparum* has a high predictive value for clinical efficacy in falciparum malaria.

The invention relates also to combinations of a compound of formula I, or a salt thereof, with one or more other pharmaceutical active substances, in particular with one or more other compounds showing antiprotozoan activity, for example with quinine, a quinoline methanol (such as mefloquine=®Lariam), a phenanthrene methanol, such as halofantrine, a 4-aminoquinoline, such as chloroquine or amodiaquine, an 8-aminoquinoline, such as pamaquine or primaquine, an acridine, such as quinacrine, a pyrimidine, such as dihydropteroic acid or dihydrofolic acid, a pyrimethamine derivative, such as pyrimethamine or trimethoprim, a sulfonamide, such as sulfadoxine (=Fanasil), a biguanide, such as chloroguanide, a dihydrotriazine, such as cycloguanil, a sulfone, such as dapsone (DDS), benflumetol or an analogue thereof or in particular artemisin or an artemisin derivative, such as especially artemether (=[3R-(3a, 5ab, 6b, 8ab, 9a, 10a, 12b,-12aR)]-decahydro-10-methoxy-3,6,9-trimethyl-3,12-epoxy-12H-pyrano[4,3-j]-1,2-benzodioxepin); or in each case a salt thereof, if at least one salt-forming group is present.

The invention relates also to a product comprising (kit of parts) (a) an active substance of formula I, or a salt thereof, and (b) as further active components one or more other active substances (or in each case a salt thereof, provided at least one salt-forming group is present), in particular one or more other compounds with antiprotozoan activity, for example quinine, a quinoline methanol (such as metloquine=®Lariam), a phenanthrene methanol, such as halofantrine, a 4-aminoquinoline, such as chloroquine or amodiaquine, an 8-aminoquinoline, such as pamaquine or primaquine, an acridine, such as quinacrine, a pyrimidine, such as dihydropteroic acid or dihydrofolic acid, a pyrimethamine derivative, such as pyrimethamine or trimethoprim, a sulfonamide, such as sulfadoxine (=Fanasil), a biguanide, such as chloroguanide, a dihydrotriazine, such as cycloguanil, a sulfone, such as dapsone (DDS), benflumetol or an analogue thereof or in particular artemisin or an artemisin derivative, such as especially artemether (=[3R-(3a, 5ab, 6b, 8ab, 9a, 10a, 12b,-12aR)]-decahydro-10-methoxy-3,6,9-trimethyl-3,12-epoxy-12H-pyrano[4,3-j]-1,2-benzodioxepin) or in each case a salt thereof, provided at least one salt-forming group is present, in the presence or absence in each case of one or more pharmaceutically acceptable carrier materials as a combination product for administration simultaneously or at different times to a warm-blooded animal, in particular a human, in particular for administration in a regimen staggered in time such that the therapeutic efficacy against said diseases is mutually potentiated by the components administered as (a) and (b) compared with the efficacy of the individual components. The formulations of the individual active substances or fixed combinations correspond to those stated under "Pharmaceutical formulations".

With the groups of preferred compounds of formula 1 mentioned hereinafter, definitions of substituents from the general definitions mentioned hereinbefore may reasonably be used, for example, to replace more general definitions with more specific definitions or especially with definitions characterized as being preferred; in each case, the definitions described hereinbefore as being preferred or exemplary are preferred.

A compound of formula I is preferred wherein R is unsubstituted or mono-, di-, or trisubstituted $C_1-C_8$alkyl, the substituents being selected from amino, hydroxy and guanidino and not bonded in position 1 of the alkyl radical, and X is halogenphenyl, in particular 4-chorophenyl, or a salt thereof.

Stronger preference is for a compound of formula I wherein R is $C_1-C_8$alkyl, in particular methyl, n-butyl, sec-butyl, n-pentyl or n-octyl, and X is 4-chlorophenyl, or a salt thereof.

Particular preference is for a compound of formula I wherein R is pentyl or butyl, in particular n-butyl, sec-butyl or n-pentyl, and X is 4-chlorophenyl, or a salt thereof.

Strongest preference is for a compound of formula I wherein R is n-butyl and X is 4-chlorophenyl, or a salt thereof.

The invention relates especially to the compounds and methods described in the examples, and to pharmaceutical compositions and methods for their preparation.

The invention relates very especially to a compound of formula I, in particular to a compound of formula I defined hereinbefore as being preferred, in essentially pure form.

PREPARATION PROCESSES

The compounds of formula I, or salts thereof, can be prepared according to methods which are known per se, but which are novel at least by virtue of the novelty of the compounds of formula I, especially by either a) condensing a compound of formula II,

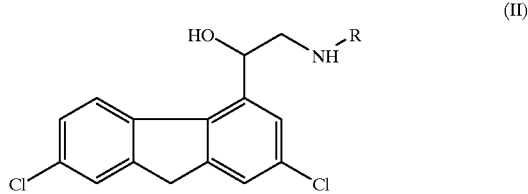

(II)

wherein R is as defined for a compound of formula I, with an aldehyde of formula III,

(III)

wherein X is as defined for compounds of formula I, or
b) adding to an oxiran of formula IV

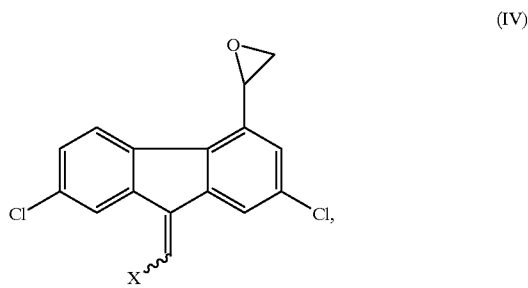

(IV)

wherein X is as defined for compounds of formula I, an amine of formula V,

R—NH₂ (V)

wherein R is as defined for a compound of formula I,
  wherein any free functional groups which are present in one of the educts of formula II in method a) or in one of the educts of formula IV and/or V in method b), and which are not supposed to take part in the reaction, are present in protected form if necessary, and any protecting groups present are removed;
  and, if so desired, reacting any free compound of formula I resulting from the procedures described under a) or b) to form its salt or any resulting salt of a compound of formula I to form either a free compound of formula I or another salt of a compound of formula I, or separating into its isomers a compound of formula I that is present as an isomeric mixture.

DETAILED DESCRIPTION OF THE PREFERRED PROCESS STEPS

Method a) The reaction preferably takes place in the presence of a base, for example a basic metal hydroxide, such as an alkali metal hydroxide, preferably sodium hydroxide, especially at a temperature between 0° C. and the reflux temperature of the reaction mixture, especially at about 20 to 40° C., in a suitable solvent, such as an anhydrous alcohol, for example ethanol.

Method b) The reaction preferably takes place in a suitable solvent, for example an alcohol, such as ethanol or preferably 2-propanol, especially at elevated temperature, for example between 25° C. and the reflux temperature of the reaction mixture, especially at reflux temperature.

Protecting groups

If one or more additional functional groups, for example carboxy, hydroxy, amino or mercapto, have to be present in a compound of formula II or a compound of formula IV and/or V in protected form, because they are not supposed to take part in the reaction, one or more of the protecting groups usually used in synthesis are added. The protecting groups may already be present in precursors and should protect the functional groups concerned against unwanted secondary reactions, such as acylations, etherifications, esterifications, oxidations, solvolysis, and similar reactions. These protecting groups may already be present at the precursor stage and are intended to protect the functional groups concerned against unwanted secondary reactions such as acylation, etherification, esterification, oxidation, solvolysis etc. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. A person skilled in the art knows, or can easily establish, which protecting groups are suitable with the reactions mentioned hereinabove and hereinafter.

The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/I, Georg Thieme Verlag, Stuttgart 1974, in H.-D. Jakubke and H. Jescheit, "Aminosauren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide und Derivate" (Chemistry of carbohydrates: monosaccharides and derivatives), Georg Thieme Verlag, Stuttgart 1974.

Protecting groups which are not components of the desired end-product of formula I, typically the carboxy, amino, and/or hydroxy protecting groups, are removed in a manner known per se, for example by solvolysis, especially hydrolysis, alcoholysis, or acidolysis, or by reduction, especially by hydrogenolysis or other methods of reduction, as well as photolysis, where applicable in gradual steps or simultaneously; enzymatic methods may also be used. The removal of protecting groups is described for example in the reference works mentioned hereinabove in the section on "Protecting groups".

Further process measures

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, and/or solvent distribution. This separation may take place either at the level of one of the starting compounds or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

Salts of compounds of formula I with one salt-forming group may be prepared in a manner known per se. Acid addition salts of compounds of formula I may thus be obtained for example by treatment with an acid or with a suitable anion exchange reagent.

Salts can be reacted to form free compounds in customary manner, for example by treating with a suitable basic agent, for example with alkali metal carbonates, hydrogen carbonates or hydroxides, for example potassium carbonate or sodium hydroxide, or they may be converted to other salts, for example by crystallization from a solution in the presence of an acid with an anion other than that of the original acid addition salt from a suitable solvent.

General process conditions

All process steps described here can be carried out under reaction conditions known per se, preferably under those specifically mentioned, in the absence of or usually in the presence of solvents or diluents, preferably such as are inert to the reagents used and able to dissolve these, in the absence or presence of catalysts, condensing agents or neutralizing agents, depending on the type of reaction and/or reactants at reduced, normal, or elevated temperature, for example in the range from −100° C. to about 190° C., preferably from about −80° C. to about 150° C., for example at −80 to −60° C., at room temperature, at −20 to 40° C. or at the boiling point of the solvent used, under atmospheric pressure or in a closed vessel, if need be under pressure, and/or in an inert, for example an argon or nitrogen, atmosphere.

Salts of all starting compounds and intermediates may be used if these contain salt-forming groups. Salts may also be present during the reaction of such compounds, provided the reaction is not thereby disturbed.

At all reaction stages, isomeric mixtures that occur can be separated into their individual isomers, e.g. diastereomers or enantiomers, or into any mixtures of isomers, e.g. racemates or diastereomeric mixtures, typically as described under "Further process steps".

The solvents from which those suitable for the reaction in question may be selected include for example water, esters, such as lower alkyl-lower alkanoates, for example diethyl acetate, cyclic ethers, for example tetrahydrofuran, alcohols, such as methanol, ethanol or 1- or 2-propanol, nitrites, such as acetonitrile, acid amides, such as dimethylformamide, bases, such as heterocyclic nitrogen bases, for example pyridine, or mixtures of these solvents, for example aqueous solutions, unless otherwise indicated in the description of the method. Such solvent mixtures may also be used in processing, for example through chromatography or distribution.

The invention relates also to those forms of the process in which one starts from a compound obtainable at any stage as an intermediate and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described hereinabove as preferred, particularly as especially preferred, primarily preferred, and/or preferred above all.

The compounds of formula I, including their salts, are also obtainable in the form of hydrates, or their crystals may include for example the solvent used for crystallization (present as solvates).

In the preferred embodiment, a compound of formula I is prepared according to the processes and process steps defined in the Examples.

Pharmaceutical compositions and their preparation, use of compounds of formula I The present invention relates likewise to pharmaceutical compositions which comprise as active substance a compound of formula I and can be used in particular for the treatment and prophylaxis of the diseases defined in the background to the invention, such as a protozoal infection or a trematode infection, primarily malaria, especially *Malaria tropica*. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with one or more pharmaceutically acceptable carriers. The dosage of the active ingredient depends upon the disease to be treated and upon the species, its age, weight, and individual condition, the individual pharmacokinetic data, and the mode of administration.

The invention relates also to pharmaceutical compositions for use in a method for the prophylactic or especially therapeutic management of the human or animal body, to a process for the preparation thereof (especially in the form of compositions for the treatment of malaria) and to a method of prophylactic or therapeutic treatment of the diseases stated hereinbefore (especially in the previous paragraph), primarily of malaria, especially *Malaria tropica*. The invention relates also to processes and to the use of compounds of formula I for the preparation of pharmaceutical preparations which comprise as active component (active ingredient) compounds of formula I.

Preference is given to a pharmaceutical composition that is suitable for administration to a warm-blooded animal, especially a human, suffering from a disease that is attributable to a protozoal or trematode infection, especially malaria, such as *Malaria tropica*, comprising a compound of formula I, or a pharmaceutically acceptable salt thereof if salt-forming groups are present, in an amount effective for the prophylactic or therapeutic treatment of this disease, together with at least one pharmaceutically acceptable carrier.

The pharmaceutical compositions comprise from approximately 1% to approximately 95% of active ingredient, single-dose administration forms comprising in the preferred embodiment from approximately 10% to approximately 90% of active ingredient and forms that are not of single-dose type comprising in the preferred embodiment from approximately 5% to approximately 20% of active ingredient. Unit dose forms are, for example, coated and uncoated tablets, ampoules, vials, suppositories, or capsules. Further dosage forms are, for example, ointments, creams, pastes, foams, tinctures, lip-sticks, drops, sprays, dispersions, etc. Examples are capsules containing from about 0.05 g to about 1.0 g of active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient on its own or together with a carrier, for example mannitol, can be made up before use.

The pharmaceutical compositions may be sterilized and/or may comprise excipients, for example preservatives, stabilizers, wetting agents and/or emulsifiers, solubilizers, salts for regulating the osmotic pressure and/or buffers and are prepared in a manner known perse, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, for example ®Tween 80 [polyoxyethylen(20)sorbitan monooleate; trademark of ICI Americas, Inc, USA].

Suspensions in oil comprise as the oil component the vegetable, synthetic, or semi-synthetic oils customary for injection purposes. Especially suitable for such purposes are liquid fatty acid esters comprising as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene. The alcohol component of these fatty acid esters has a maximum of 6 carbon atoms and is a mono- or polyhydric, for example a mono-, di- or trihydric, alcohol, for example methanol, ethanol, propanol, butanol or pentanol or the isomers thereof, but especially glycol and glycerol. The following are therefore examples of suitable fatty acid esters: ethyl oleate, isopropyl myristate, isopropyl palmitate, polyoxyethylene glycerol trioleate, unsaturated polyglycolized glycerides prepared by alcoholysis of apricot seed oil and constituted from glycerides and polyethylene glycol ester; saturated polyglycolized glycerides prepared by alcoholysis of TCM and constituted from glycerides and polyethylene glycol ester and/or triglycerides of saturated fatty acids of chain length $C_8$ to $C_{12}$, but especially vegetable oils such as cottonseed oil, almond oil, olive oil, castor oil, sesame oil, soybean oil and more especially groundnut oil.

The manufacture of injectable preparations is usually carried out under sterile conditions, as is the filling, for example, into ampoules or vials, and the sealing of the containers.

Pharmaceutical compositions for oral administration can be obtained, for example, by combining the active ingredient with one or more solid carriers, if need be granulating a resulting mixture, and processing the mixture or granules, if desired, to form tablets or tablet cores, if need be by the inclusion of additional excipients.

Suitable carriers are especially fillers, such as sugars, for example lactose, saccharose, mannitol or sorbitol, cellulose preparations, in particular microcrystalline cellulose, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores may be provided with suitable, if need be enteric, coatings, using inter alia concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Orally administrable pharmaceutical compositions also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and if need be stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Other oral dosage forms are, for example, syrups prepared in customary manner which comprise the active ingredient, for example, in suspended form and in a concentration of about 5% to 20%, preferably about 10%, or in a similar concentration that provides a suitable single dose, for example, when administered in measures of 5 or 10 ml. Also suitable are, for example, powdered or liquid concentrates for the preparation of shakes, for example in milk. Such concentrates may also be packaged in single dose quantities.

Suitable rectally administrable pharmaceutical compositions are, for example, suppositories that comprise a combination of the active ingredient and a suppository base. Suitable suppository bases are, for example, natural or synthetic triglycerides, paraffin hydrocarbons, polyethylene glycols or higher alkanols.

The aqueous solutions suitable for parenteral administration are especially those of an active ingredient in water-soluble form, for example in the form of a water-soluble salt, or aqueous injection suspensions that contain viscosity-increasing substances, for example sodium carboxymethylcellulose, sorbitol and/or dextran, and, if need be, stabilizers. The active ingredient, if need be together with excipients, can also be in the form of a lyophilizate and can be made into a solution before parenteral administration by the addition of suitable solvents.

Solutions such as are used, for example, for parenteral administration can also be employed as infusion solutions.

Preferred preservatives are, for example, antioxidants, such as ascorbic acid, or microbicides, such as sorbic acid or benzoic acid.

The invention likewise relates to a process or a method of therapeutic or prophylactic treatment of the disease conditions defined hereinbefore, in particular malaria, more especially *Malaria tropica*. The compounds of formula I can be administered as such or in the form of pharmaceutical compositions, prophylactically or therapeutically, preferably in an amount effective against the said diseases, to a warm-blooded animal requiring such treatment, for example to a human, the compounds especially being used in the form of pharmaceutical compositions. In the case of an individual having a bodyweight of about 70 kg the daily dosage administered is from approximately 0.01 g to approximately 5 g, preferably from approximately 0.05 g to approximately 2 g, of a compound of the present invention, preferably divided into 3 to 5, especially 4, separate doses.

The present invention relates especially also to the use of a compound of formula I, or a pharmaceutically acceptable salt thereof, especially a compound of formula I or a pharmaceutically acceptable salt thereof which is said to be preferred, as such or in the form of a pharmaceutical formulation with at least one pharmaceutically acceptable carrier for the therapeutic or prophylactic treatment of one or more of the diseases stated hereinbefore, especially malaria, more especially *Malaria tropica*.

The preferred dose quantity, composition, and preparation of pharmaceutical formulations (medicines) which are to be used in each case are described above.

A compound of formula I, or a salt thereof, (=component (a)) may be formulated or used in the said pharmaceutical compositions, processes for the preparation of pharmaceutical compositions, methods and/or uses alone or in combination with one or more other active ingredients (component (s) (b)), especially those mentioned in the background to the invention, components (a) and (b) being formulated in combinations either together in a fixed combination or separately in a product comprising (kit of parts) (a) an active ingredient of formula I, or a salt thereof, and (b) as further active component one or more additional active ingredients, as defined hereinbefore, especially for administration in a regimen staggered in time such that the therapeutic efficacy against said diseases is mutually potentiated by the components administered as (a) and (b) compared with the efficacy of the components administered separately.

Starting materials

New starting materials and/or intermediates, as well as processes for the preparation thereof, are likewise the subject of this invention. In the preferred embodiment, such starting materials are used and reaction conditions so selected as to enable the preferred compounds to be obtained.

The subject of the present invention is in particular a starting material of formula II, wherein R has the meaning given in the definition of a compound of formula I. Preference is for a compound of formula II in which R is as defined for the compounds of formula I which are stated to be preferred. A compound of formula II wherein R is butyl, in particular n-butyl, is especially preferred.

The starting material of formula II can be prepared from an oxiran of formula VI,

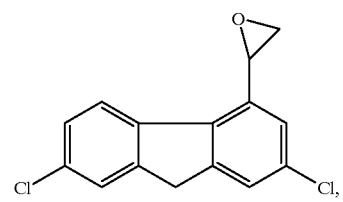

(VI)

by reacting this in a manner analogous to the conditions stated under method b) with, instead of the oxiran of formula IV stated therein, an amine of formula V as defined therein.

The oxiran of formula IV can be prepared from an oxiran of formula VI, as shown hereinbefore, by reaction with an aldehyde of formula III, as defined hereinbefore under method a), in a manner analogous to the conditions stated under method a), when a compound of formula VI is used instead of a compound of formula II.

A compound of formula VI is known or prepared according to methods known per se (see for example the Chinese patent application CN 104 45 35 A (published on May 30, 1990) or Atkinson et al., J. Med. Chem. 11, 1223 (1968) and Atkinson et al., J. Med. Chem. 17, 1009 (1974)).

Amines of formula V and aldehydes of formula III are known, capable of being prepared according to methods known per se, or commercially obtainable.

EXAMPLES

The following Examples serve to illustrate the invention without limiting the scope thereof.
Starting materials 4 (see Table 1):
A) 2-Methylamino-1-(2,7-dichloro-9H-fluoren-4yl)ethanol (4a)

A mixture of 5.0 g 2,7-dichloro-9H-fluoren-4-oxiran (1), 25 g methylamine (33% solution in ethanol) and 20 ml ethanol is refluxed for 2 days. The reaction mixture is cooled to room temperature and filtered. The filter cake is washed with ethanol and dried under a vacuum, and a mixture of 4a and bis-[2-(2,7-dichloro-9H-fluoren-4-yl)-2-nydroxy] ethylmethylamine obtained: $^1$H-NMR (300 MHz, CDCl$_3$): 2.4 and 2.55 (two singlets, N—Ch$_3$, in each case 4a and bis-[2-(2,7-dichloro-9H-fluoren-4-yl)-2-hydroxy] ethylmethylamine); 2.6–3.0 (m, CH$_2$—N); 3.8 and 3.9 (two singlets, C-9-H of fluorenyl groups); 5.4 and 5.5 (two double doublets, CH—O); 7.1–7.7 (m, aromatic protons).

The following starting materials are prepared in an analogous manner (see Table 1)
B) 2-n-Butylamino-1-(2,7-dichloro-9H-fluoren-4yl)ethanol (4b):

(with n-butylamine instead of methylamine as educt) $^1$H-NMR (200 Mhz, CDCl$_3$): 0.9 (t, 3H, CH$_3$—CCC—N); 1.2–1.6 (m, 4H, CH$_2$—CH$_2$—C—C—N); (2.6–2.8 (m,3H, CH—N—CH$_2$); 3.1 (dd, 12 Hz, 3Hz, 1H, CH—N); 3.9 (s, 2H, C-9-H); 5.4 (dd,1H, 4Hz, 8Hz, CH—O); 7.3–7.8 (m, 5H).
C) 2-n-Hexylamino-1-(2.7-dichloro-9H-fluoren-4yl)ethanol (4d):

(with n-hexylamine instead of methylamine as educt) $^1$H-NMR (300 Mhz, CDCl$_3$): 0.8 (t, 3H, N—C—C—C—C—C—CH$_3$); 1.1–1.3 (m, 6H, N—C—CH$_2$CH$_2$CH$_2$—C); (1.4, m, 2H, N—C—CH$_2$—); 2.5–2.7 (m, 3H, CH—N—CH$_2$); 2.95 (dd, 1 H, CH—N); 3.75 (s, 2H, C-9-H); 5.35 (dd, 1 H, O—CH—); 7.25 (d with long range coupling, 8Hz, 1 H, C-6-H); 7.32, 7.43 (two singlets with long range coupling, 1H, 1H, C-1-H, C-3-H); 7.56 (s with long range coupling, 1H, C-8-H); 7.58 (d, 8Hz, C-5-H).
D) 2-n-Octylamino-1-(2.7-dichloro-9H-fluoren-4yL)ethanol (4e):

(with n-octylamine instead of methylamine as educt) $^1$H-NMR (300 Mhz, CDCl$_3$): 0.8 ppm (t, 3H, CH$_3$); 1.1–1.3 (m, 10H, NCC(CH$_2$)$_5$—C); 1.4 (m, 2H, N—C—CH$_2$—); 2.5–2.7 (m, 3H, CH—N—CH$_2$); 3,0 (dd, 1H, CH—N); 3.8 (s, 2H, C-9-H); 1.4 (m, 2H, N—C—CH$_2$—); 3.8 (s, 2H, C-9-H); 5.35 (dd, 1 H, O—CH—); 7.25 (d with long range coupling, 8Hz, 1 H, C-6-H); 7.58 (s with long range coupling, 1 H, C-8-H); 7.60 (d, 8Hz, C-5-H).
E) 2-[2-(2-Hydronxy]ethoxyethylamino-1-(2.7-dichloro-9H-fluoren-4yl)ethanol (4f):

(with 2-(2-aminoethoxy)ethanol (Fluka, Buchs, Switzerland) as educt instead of methylamine) $^1$H-NMR (300 MHz, CDCl$_3$): 2.0 ppm (broad, 1H, OH); 2.7–3.0 (m, 4H, CH$_2$NCH$_2$); 3.6 (m, 4H, C—CH$_2$OCH$_2$—C); 3.75 (m, 2H, CH$_2$—OH); 3.85 (s, 2H, C-9-H); 5.5 (dd, 1 H, O—CH); 7.3 (dm, 1 H, C-6-H); 7.4 and 7.5 (two s, in each case 1 H, C-1,3-H); 7.65 (split s, 1 H, C-8-H); 7.7 (d, 1 H, C-5-H).

TABLE 1

Starting materials

| Structure | R = |
|---|---|
| HO—CH(—)—CH$_2$—NH—R on 2,7-dichlorofluorene (4) | 4a CH$_3$<br>4b CH$_2$CH$_2$CH$_2$CH$_3$<br>4c CH$_2$CH$_2$CH$_2$HC$_2$CH$_3$<br>4d CH$_2$CH$_2$CH$_2$CH$_2$CH$_2$CH$_3$<br>4e CH$_2$CH$_2$CH$_2$CH$_2$CH$_2$CH$_2$CH$_2$CH$_3$<br>4f CH$_2$CH$_2$—O—CH$_2$CH$_2$—OH |

EXAMPLES
(end-products) (see Table 2)

Example 1
2-Methylamino-1-[2,7-dichloro-9-(4-chlorobenzylidene)-9H-fluoren-4yl]ethanol (5a)

Preparation analogous to that under Example 2, starting from 4a instead of 4b. $^1$H-NMR (300 MHz, CDCl$_3$): 2.3 ppm (broad s, 3H, N—Ch$_3$); 1.3–2.0 (broad s, 2H, NH, OH); 2.45–2.6 (m, 1 H, CH—N); 2.7–2.85 (m, 1 H, CH—N), 5.2 (br. d, 1 H, CH—O); 7.0–7,6 (m, 10OH).

Example 2
"N-Desbutyl benflumetol"=2-n-butylamino-1[2,7-dichloro-9-(4-chlorobenzylidene)-9H-fluoren-4yl]ethanol (5b)

A suspension of 6.47 g 4b in 123 ml absolute ethanol is treated with 4.28 g 4-chlorobenz-aldehyde and 0.78 g sodium hydroxide. The suspension is agitated for 30 hours at 30° C. The mixture is filtered, the filter cake washed with ethanol and dried under a vacuum, the N-desbutyl benflumetol being obtained as a mixture of isomers (E, Z). $^1$H-NMR (200 Mhz, C$_6$D$_6$): 0.8 ppm (m, 3H, CH3); 1.2 (m, 4H, N—C—CH$_2$CH$_2$—C); 2.2–2.4 (m, 2H, O—C—C—N—CH$_2$); 2.4–2.6 (m) and 2.75 (dd) je 1 H (O—C—CH$_2$—N); 5.4 (dd, 9Hz, 2.7Hz, 1 H, CH—O); 7.0–8.1 (m, 10H).

Example 3
2-n-Octylamino-1-[2.7-dichloro-9-(4-chlorobenzylidene)-9H-fluoren-4yl]ethanol (5e)

Preparation analogous to that under Example 2 starting from 4e instead of 4b; after purification on silica gel (eluant: toluene/ethanol 19:1, v/v) the title is obtained as an oil which crystallizes out when left to stand: $^1$H-NMR (300 MHz, CDCl$_3$): 0.8 ppm (t, 3H, CH$_3$); 1.2 (s br., 10H, N—CC—(CH$_2$)$_5$—C); 1.4 (m, 2H, N—C—CH$_2$—); 1.6–2.3 (br., 2H, NH, OH); 2.5–2.7 (m, 3H, CH—N—C$_2$); 2.95 (dd, 1 H, CH—N); 5.3 (m, 1 H, O—CH); 7.2–7.7 (m, 10H, aromatic a vinylic CH).

Example 4
2-[2-(2-Hydroxy)ethoxy]ethylamino-1-[2.7-dichloro-9-(4-chlorobenzylidene)-9H-fluoren-4yl]ethanol (5f)

Preparation analogous to that under Example 2 starting from 4f instead of 4b; title compound (obtained after chromatography on silica gel column, eluant toluene/ethanol 9:1, v/v): $^1$H-NMR (300 Mhz, CDCl$_3$): 1.5–2.2 ppm (br., 3H, OH, NH); 2.5–3.0 (m, 4H, CH$_2$—N—Ch$_2$); 3.5 (m, 4H, , CH$_2$—O—CH$_2$); 3.7 (m, 2H, CH$_3$—OH); 5.4 (d, br., 1 H, Ar—CH—O); 7.3–7.8 (m, 10H, aromatic and vinylic CH).

Example 5
2-n-Pentylamino-1-[2.7-dichloro-9-(4-chlorobenzylidene)-9H-fluoren-4yl]ethanol (5e)

A mixture of 0.76 g 2.7-dichloro-9-(4-chlorobenzylidene)-9H-fluoren-4-oxiran, 0.77 g n-pentylamine and 7 g 2-propanol is refluxed for 26 hours. The mixture is cooled and agitated for a further two days at room temperature. The product is filtered off, washed with 2-propanol, and dried under a vacuum: $^1$H-NMR (300 MHz, CDCl$_3$): 0.8 ppm (t, 3H, CH$_3$); 1.2 (m, 4H, O—C—C—CH$_2$CH$_2$—C); 1.4 (m, 2H, O—C—CH$_2$—CCC); 1.6–2.4 (br., 2H, NH, OH); 2.5–2.7 (m, 3H, CH—N—C$_2$); 3.0 (dd, 1 H, CH—N); 5.3 (dd, 1 H, O—CH); 7.2–7.7 (m, 1H, aromatic and vinylic CH).

The starting material is prepared as follows:
5a) 2,7-Dichloro-9-(4-chlorobenzylidene)-9H-fluoren-4-oxiran 2:

A mixture of 20 g 2.7-dichloro-9H-fluoren-4-oxiran, 17.7 g 4-chlorobenzaldehyde, 500 ml ethanol and 27.5 g sodium hydroxide is agitated for 18 hours at 25° C. (initially under cooling). The yellow solid substance obtained is filtered off, washed with water, and the title compound thus obtained. $^1$H-NMR (300 MHz, CDCl$_3$): 2.8 and 3.4 (td, t, in each case 1 H, oxiran—CH$_2$O—); 4.4 (br. s, 1 H, Ar—CH(—C)—O); 7.3–7.8 (m, 10H, aromatic and vinylic CH including br. s at 7.5 ppm for C$_6$H$_4$—Cl).

Example 6
Comparison of the efficacy of benflumetol (2-(di-n-butylamino)-1-[2,7-dichloro-9-(4-chlorobenzylidene)-9H-fluoren-4-yl]ethanol and 2-alkylamino-1-[2,7-dichloro-9-(4-choro-benzylidene]-9H-fluoren-4-yl]ethanols against Plasmodium falciparum in vitro:

The study is carried out in Mae Sot, a province in north-west Thailand close to Myanmar. The *Plasmodium falciparum* isolates used for the study come from patients who have clinically manifest malaria and attend the VBC Unit Malaria Clinic in Mae Sot for diagnosis and treatment. The test for efficacy is carried out with blood samples obtained by finger pricks (in accordance with the WHO Standard Microtest Method for studying the inhibition of schizont maturation, see Wemsdorfer, W. H., and Payne, D. (1988), Drug Sensitivity Tests. In: Wemsdorfer, W. H., and McGregor, I. A. (Editors), Malaria: Principles and practice of malariology; Churchill Livingstone, Edinburgh). The tests are carried out in parallel with benflumetol and the 2-alkylamino-1-[2,7-dichloro-9-(4-chlorobenzylidene]-9H-fluoren-4-yl)ethanols in concentrations between 3 and 3000 nmol/l in blood medium mixture (BMM) using materials from the WHO Standard Test Kit supplied by the WHO Regional Office for the Western Pacific, Manila, except for the predosed microtitre plates, which are prepared in the laboratory of the Institute of Specific Prophylaxis and Tropical Medicine, University of Vienna, Austria.

The procedure for determining parasitaemia before incubation follows the WHO Standard Method (WHO (1991), Basic malaria microscopy. Part I; WHO, Geneva). The schizont titres are determined as described in Wemsdorfer and Payne (1988) (see above).

The statistical analysis of the data was carried out according to log-concentration/response probit analysis (Litchfield & Wilcoxon (1949), J. Exp. Pharmacol. 89, 99–113). This method is based on the least-squares procedure and is the most widely accepted method for the analysis of dose-response studies. A computer adaptation of the method (Wemsdorfer & Wemsdorfer, *Mitteilungen der Österreichischen Gesellschaft für Tropenmedizin und Parasitologie* 17, 221–228) is used for data processing.

Results:

Example 6.1
Comparison of the efficacy of benflumetol and N-desbutyl benflumetol (5b. 2-(n-butylamino)-1-[2,7-dichloro-9-(4-chlorobenzylidene)-9H-fluoren-4-yl]ethanol):

TABLE 2

Examples

| Structure | R = |
|---|---|
| [fluorene structure with HO-CH-CH2-NH-R substituent; 2,7-dichloro-9-(4-chlorobenzylidene)-9H-fluoren-4-yl] 5 | 5a CH$_3$<br>5b CH$_2$CH$_2$CH$_2$CH$_3$<br>5c CH$_2$CH$_2$CH$_2$CH$_2$CH$_3$<br>5d CH$_2$CH$_2$CH$_2$CH$_2$CH$_2$CH$_3$<br>5e CH$_2$CH$_2$CH$_2$CH$_2$CH$_2$CH$_2$CH$_2$CH$_3$<br>5f CH$_2$CH$_2$—O—CH$_2$CH$_2$—OH |

None of the 58 *Plasmodium falciparum* isolates studied shows schizont maturation at concentrations of benflumetol above 300 nmol/l, and the great majority of isolates (97%) are completely inhibited at 300 nmol/l benflumetol. Not one of the isolates shows schizont maturation at a concentration of 300 nmol/l N-desbutyl benflumetol, and the great majority of isolates are completely inhibited even at 100 nml/l N-desbutyl bentlumetol.

The response parameters for benflumetol are shown in Table 3 and those for N-desbutyl benflumetol in Table 4. The $\chi^2$ for heterogeneity shows an acceptable agreement of the observed data with the regression lines. This is also apparent in the relatively narrow confidence limits (95%).

There are major differences in the sensitivity of isolates to either benflumetol or n-desbutyl-benflumetol, for example an $EC_{50}$ (dose producing 50% inhibition versus controls not given active substance) of 24.44 nmol/l for benflumetol and 4.36 nmol/l for n-desbutylbenflumetol. Similarly, the $EC_{99}$ (99% inhibition versus controls not given active substance), which is the most important indicator for clinical efficacy of benflumetol (371.59 nmol/l) in non-immune persons is around 8 (eight) times higher than that for n-desbutylbenflumetol (45.72 nmol/l).

Statistical comparison according to Litchfield & Wilcoxon shows that the regression lines run parallel within the limits of experimental error because the slope ratio (SR= 1.1718) is smaller than the factor of the slope ratio ($f_{SR}$= 1.3063). Since the "power ratio" (PR=5.6083) is also greater than the factor of the power ratio ($f_{PR}$=1.4849), the difference in efficacy between benflumetol and n-desbutylbenflumetol is statistically highly significant.

The 58 $EC_{50}$ pairs are tested for correlation. With a correlation coefficient of 0.7308, the result is highly significant (p<0.000003). This applies also to the 58 $EC_{90}$ pairs (correlation coefficient 0.6768, p <0.00001).

TABLE 3

Concentration-dependent inhibitory effect of benflumetol on Plasmodium falciparum in vitro:

| Active substance concentration (nmol/l) | Inhibition of schizont maturation in % |
|---|---|
| 3.0 | 7.14 |
| 10.0 | 20.44 |
| 30.0 | 47.16 |
| 100.0 | 90.72 |
| 300.0 | 99.79 |
| 1000.0 | 100.00 |
| 3000.0 | 100.00 | n=58; a=2.2678; b=0.8548; r=0.9739; $\chi^2$ =5.6500
S=3.2009; A=1.2922; K=6; N'=116; R=333.3333333
$f_S$=1.2193; $f_{EC50}$=1.3488; $f_{EC99}$=1.7399
$EC_{50}$: mean value=24.4427 (95% confidence limits: lower 18.1217; upper 32.9685)
$EC_{99}$: mean value=371.5908 (95% confidence limits: lower 213.5703; upper 646.5307)
y=0.0997+1.8487; $R^2$=0.534

TABLE 4

Concentration-dependent inhibitory effect of N-desbutylbenflumetol (5b) on Plasmodium falciparum in vitro:

| Active substance concentration (nmol/l) | Inhibition of schizont maturation in % |
|---|---|
| 3.0 | 36.53 |
| 10.0 | 77.40 |
| 30.0 | 98.60 |
| 100.0 | 99.85 |
| 300.0 | 100.00 |
| 1000.0 | 100.00 |
| 3000.0 | 100.00 | n=58; a=3.5431; b=0.9897; r=0.9941; $\chi^2$=0.6368
S=2.7315; A=1.2727; K=5; N'=116; R=100
$f_S$=1.1962; $f_{EC50}$=1.2949; $f_{EC99}$=1.6388
$EC_{50}$: mean value=4.3583 (95% confidence limits: lower 3.3658; upper 5.6436)
$EC_{99}$: mean value=45.7213 (95% confidence limits: lower 27.8989; upper 74.9291)
Y=0.0806x+5.3769; $R^2$=0.4581

Examples 6.2 and 6.3:

In Examples 6.2 and 6.3, 34 *Plasmodium falciparum* isolates are tested. None of the 34 *Plasmodium falciparum* isolates studied shows schizont maturation at concentrations of benflumetol above 3000 nmol/l, and the great majority of isolates (96%) are completely inhibited at 300 nmol/l benflumetol.

The isolates of patients 11, 39 and 47 proved as highly resistant to mefloquine, resulting in an unacceptably high degree of heterogeneity in the data ($\chi^2$=16.153 at a maximum permissible value of 11.1). There was a positive correlation between sensitivity to mefloquine and sensitivity to benflumetol. The response of these isolates to benflumetol and the tested compounds was also relatively weak, this influence appearing to a lesser extent on the tested compounds than on benflumetol. The correlation of the response to specific pairs of active substances at the $EC_{50}$ and $EC_{90}$ values was calculated with all isolates. The compounds of Examples 6.2 and 6.3 proved more effective than benflumetol in the present test.

TABLE 5

Concentration-dependent inhibitory effect of benflumetol on Plasmodium falciparum in vitro (34-isolate test series, Examples 6.2 and 6.3):

| Active substance concentration (nmol/l) | Inhibition of schizont maturation in % |
|---|---|
| 3.0 | 7.16 |
| 10.0 | 18.40 |
| 30.0 | 42.75 |
| 100.0 | 90.74 |
| 300.0 | 96.25 |
| 1000.0 | 99.92 |
| 3000.0 | 100.00 | n=34; a=2.3498; b=0.7956; r=0.9814; $\chi_2$=3.6652
S=3.4906; A=1.2825; K=7; N'=68; R=1000
$f_S$=1.2952; $f_{EC50}$=1.5218; $f_{EC99}$=2.0934
$EC_{50}$: mean value=27.9715 (95% confidence limits: lower 13.3802; upper 42.5678)
$EC_{99}$: mean value=520.7651 (95% confidence limits: lower 248.7678; upper 1090.1581)

Example 6.2

Comparison of the efficacy of benflumetol and 2-methylamino-1-[2,7-dichloro-9-(4-chlorobenzylidene)-9H-fluoren-4-yl]aethanol (5a):

The response parameters for benflumetol are defined in Table 5 (see above) and those for compound 5a in Table 6. The $\chi^2$ for heterogeneity shows an acceptable agreement between the data observed and the regression lines.

Not one of the isolates shows schizont maturation at a concentration of 1000 nmol/l 5a, and the great majority of isolates (96%) are completely inhibited even at 100 nml/l.

There are major differences in the sensitivity of the isolates to either benflumetol or compound 5a. For example, the $EC_{99}$ (99% inhibition versus controls not given active substance), which is the most important indicator for clinical efficacy of compound 5a (87.03 nmol/l) in non-immune persons, amounts to only about one fifth of that for benflumetol (422.49 nmol/l), i.e. the same effect on *Plasmodium falcipanrum* was attained with substance 5a at approximately one fifth the dose.

Statistical comparison according to Litchfield & Wilcoxon shows that the regression lines run parallel within the limits of experimental error because the slope ratio (SR= 1.2483) is smaller than the factor of the slope ratio ($f_{SR}$= 1.6193). Since the "power ratio" (PR=2.8898) is also greater than the factor of the power ratio ($f_{PR}$=1.9077), the difference in efficacy between benflumetol and compound 5a is statistically significant.

The 34 $EC_{50}$ pairs are tested for correlation. With a correlation coefficient of 0.6430, the result is significant. This applies also to the 34 $EC_{90}$ pairs with a correlation coefficient of 0.7697.

TABLE 6

Concentration-dependent inhibitory effect of 2-methylamino-1-[2,7-dichloro-9-(4-chlorobenzylidene)-9H-fluoren-4-yl]ethanol (5a) on Plasmodium falciparum in vitro:

| Active substance concentration (nmol/l) | Inhibition of schizont maturation in % |
|---|---|
| 3.0 | 13.12 |
| 10.0 | 51.92 |
| 30.0 | 83.14 |
| 100.0 | 95.81 |
| 300.0 | 97.06 |
| 1000.0 | 100.00 |
| 3000.0 | 100.00 | n=34; a=3.3024; b=0.7216; r=0.9754; $\chi_2$=3.8764

S=3.9675; A=1.4328; K=6; N'=102; R=333.333

$f_S$=1.3455; $f_{EC50}$=1.4593; $f_{EC99}$=2.2105

$EC_{50}$: mean value=10.5116 (95% confidence limits: lower 7.2030; upper 15.3400)

$EC_{99}$: mean value=264.0564 (95% confidence limits: lower 119.4579; upper 583.6850)

Compound 5a shows marked activity against malaria and is about four times as effective as benflumetol. In addition, the sensitivity of *Plasmodium falciparum* to compound 5a has a steeper incremental function (S) than benflumetol.

Example 6.3

Comparison of the efficacy of benflumetol and 2-n-pentylamino-1-[2,7-dichloro-9-(4-chlorobenzylidene)-9H-fluoren-4-yl]ethanol (5c):

The response parameters for benflumetol are defined in Table 5 (see above) and those for compound 5c in Table 7. The $\chi^2$ for heterogeneity shows an acceptable agreement between the data observed and the regression lines.

Not one of the isolates shows schizont maturation at a concentration of 3000 nmol/l 5c, and the great majority of isolates (95%) are completely inhibited even at 100 nml/l 5c.

There are major differences in the sensitivity of the isolates to either benflumetol or compound 5c. For example, the $EC_{99}$ (99% inhibition versus controls not given active substance), which is the most important indicator for clinical efficacy of compound 5c (105.04 nmol/l) in non-immune persons, is about 4 (four) times lower than that for benflumetol (422.49 nmol/l), i.e. the same effect on *Plasmodium falciparum* is attained with substance 5c with a dose about 75% lower than that used with benflumetol.

Statistical comparison according to Litchfield & Wilcoxon shows that the regression lines run parallel within the limits of experimental error because the slope ratio (SR= 1.3277) is smaller than the factor of the slope ratio ($f_{SR}$= 1.5017). Since the "power ratio" (PR=2.0724) is also greater than the factor of the power ratio ($f_{PR}$=1.7033), the difference in efficacy between benflumetol and compound 5c is statistically significant.

The 34 $EC_{50}$ pairs are tested for correlation. With a correlation coefficient of 0.6044, the result is significant. This applies also to the 34 $EC_{90}$ pairs with a correlation coefficient of 0.8796.

TABLE 7

Concentration-dependent inhibitory effect of 2-pentylamino-1-[2,7-dichloro-9-(4-chlorobenzylidene)-9H-fluoren-4-yl]ethanol (5c) on Plasmodium falciparum in vitro:

| Active substance concentration (nmol/l) | Inhibition of schizont maturation in % |
|---|---|
| 3.0 | 6.83 |
| 10.0 | 36.40 |
| 30.0 | 81.18 |
| 100.0 | 94.78 |
| 300.0 | 96.96 |
| 1000.0 | 99.61 |
| 3000.0 | 100.00 | n=34; a=3.0184; b=0.7436; r=0.9696; $\chi^2$=4.7652

S=3.8093; A=1.3296; K=6; N'=68; R=1000

$f_S$=1.3446; $f_{EC50}$=1.5672; $f_{EC99}$=2.2892

$EC_{50}$: mean value=14.3678 (95% confidence limits: lower 9.1681; upper 22.5167)

$EC_{99}$: mean value=328.1566 (95% confidence limits: lower 143.3474; upper 751.2290)

Compound 5c shows activity per se against malaria and is about five times as effective as benflumetol.

It is shown that exchanging the dibutylamino group in benflumetol for a monoalkylamino group results in benflumetol derivatives which show an activity that appears to be markedly superior.

Example 7

Tablets

The active substance desbutyl benflumetol is passed through a (60 mesh) sieve and, after mixing, compressed to form tablets of the following composition:

| | |
|---|---|
| Desbutyl benflumetol | 120 mg |
| Microcrystalline cellulose | 100 mg |
| Corn starch | 160 mg |
| Sodium carboxymethyl starch | 12 mg |
| Highly dispersed silica | 3 mg |
| Magnesium stearate | 5 mg |
| Total | 400 mg |

What is claimed is:

1. A compound of formula I

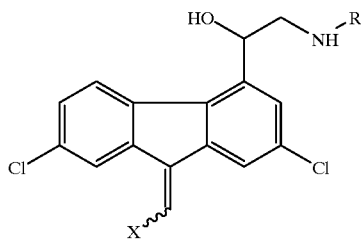

wherein R is an alkyl unsubstituted or substituted by one or more polar substituents or an alkenyl unsubstituted or substituted by one or more polar substituents, and X is unsubstituted or substituted aryl, or a salt thereof.

2. A compound of claim 1 wherein R is unsubstituted or mono-, di-, or trisubstituted $C_1$–$C_8$alkyl, the substituents being selected from amino, hydroxy and guanidino and not bonded in position 1 of the alkyl radical, and X is halogenphenyl, or a salt thereof.

3. A compound wherein R is $C_1$–$C_8$alkyl, and X is 4-chlorophenyl, or a salt thereof.

4. A compound of claim 3 wherein the $C_{1-C8}$ alkyl is selected from methyl, n-butyl, sec-butyl, n-pentyl or n-octyl.

5. The compound wherein R is n-butyl and X is 4-chlorophenyl, or a salt thereof.

6. A combination of a compound of formula I, or a salt thereof, according to claim 1 with one or more other pharmaceutical active substances, or in each case a salt thereof if at least one salt-forming group is present in each case.

7. A combination of a compound of formula I, or a salt thereof, according to claim 2 with one or more other pharmaceutical active substances, or in each case a salt thereof if at least one salt-forming group is present in each case.

8. A combination of a compound of formula I, or a salt thereof, according to claim 3 with one or more other pharmaceutical active substances, or in each case a salt thereof if at least one salt-forming group is present in each case.

9. A combination of a compound of formula I, or a salt thereof, according to claim 5 with one or more other pharmaceutical active substances, or in each case a salt thereof if at least one salt-forming group is present in each case.

10. A product comprising (a) an active substance of formula I, or a salt thereof, according to claim 1, and (b) as a further component one or more further active substances, or a salt thereof in each case if at least one salt-forming group is present, in the presence or absence of one or more pharmaceutically acceptable carriers as a combination product for administration simultaneously or at different times to a warm-blooded animal.

11. A product comprising (a) an active substance of formula I, or a salt thereof, according to claim 2, and (b) as a further component one or more further active substances, or a salt thereof in each case if at least one salt-forming group is present, in the presence or absence of one or more pharmaceutically acceptable carriers as a combination product for administration simultaneously or at different times to a warm-blooded animal.

12. A product comprising (a) an active substance of formula I, or a salt thereof, according to claim 3, and (b) as a further component one or more further active substances, or a salt thereof in each case if at least one salt-forming group is present, in the presence or absence of one or more pharmaceutically acceptable carriers as a combination product for administration simultaneously or at different times to a warm-blooded animal.

13. A product comprising (a) an active substance of formula I, or a salt thereof, according to claim 5, and (b) as a further component one or more further active substances, or a salt thereof in each case if at least one salt-forming group is present, in the presence or absence of one or more pharmaceutically acceptable carriers as a combination product for administration simultaneously or at different times to a warm-blooded animal.

14. A pharmaceutical composition comprising a compound of formula I or a pharmaceutically acceptable salt thereof according to claim 1, together with at least one pharmaceutically acceptable carrier.

15. A pharmaceutical composition comprising a compound of formula I or a pharmaceutically acceptable salt thereof according to claim 2, together with at least one pharmaceutically acceptable carrier.

16. A pharmaceutical composition comprising a compound of formula I or a pharmaceutically acceptable salt thereof according to claim 3, together with at least one pharmaceutically acceptable carrier.

17. A pharmaceutical composition comprising a compound of formula I or a pharmaceutically acceptable salt thereof according to claim 5, together with at least one pharmaceutically acceptable carrier.

18. A method for the therapeutic or prophylactic treatment of a protozoan or a trematode disease in a subject in need of such treatment comprising administering to the subject a therapeutically effective amount of a compound according to claim 1.

19. A method for the preparation of a compound of formula I according to claim 1, or a salt thereof, comprising a) condensing a compound of formula II

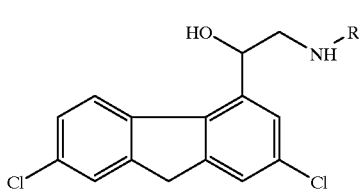

wherein R is as defined for a compound of formula I, with an aldehyde of formula III,

wherein X is as defined for compounds of formula I, or b) adding to an oxiran of formula IV

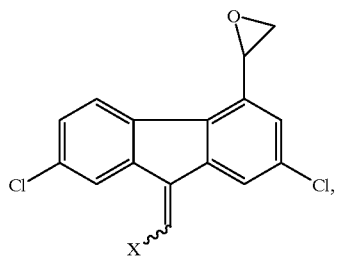

(IV)

wherein X is as defined for compounds of formula I, an amine of formula V,

R—NH$_2$  (V)

wherein R is as defined for a compound of formula I, wherein any free functional groups which are present in one of the educts of formula II in method a) or in one of the educts of formula IV and/or V in method b) and which are not supposed to take part in the reaction are present in protected form if necessary, and any protecting groups present are removed; and, if so desired, reacting any free compound of formula I resulting from the procedures described under a) or b) to form its salt or any resulting salt of a compound of formula I to form either a free compound of formula I or another salt of a compound of formula I, or separating into its isomers a compound of formula I that is present as an isomeric mixture.

* * * * *

UNITED STATES PATENT AND TRADEMARK OFFICE
CERTIFICATE OF CORRECTION

PATENT NO.    : 6,329,552 B2
DATED         : December 11, 2001
INVENTOR(S)   : Thomas Allmendinger et al.

It is certified that error appears in the above-identified patent and that said Letters Patent is hereby corrected as shown below:

Column 1,
Line 58 should read -- 10-methoxy-3,6,9-trimethyl-3,12-epoxy-12H-pyrano[4,3-j]- --

Column 13,
Line 37 should read -- 2.4 and 2.55 (two singlets, N-CH$_3$, in each case 4a and --
Line 48 should read -- 1.2-1.6 (m, 4H, CH$_2$-CH$_2$-C-N); 2.6-2.8 (m, 3H, --
Line 52 should read -- C) 2-n-Hexylamino-1-(2,7-dichloro-9H-fluoren-4yl)ethanol --
Line 56 should read -- C-C-CH$_3$); 1.1-1.3 (m, 6H, N-C-C-CH$_2$CH$_2$CH$_2$-C); --
Line 63 should read -- D) 2-n-Octylamino-1-(2,7-dichloro-9H-fluoren-4yL)ethanol --

Column 14,
Line 6 should read -- E) 2-[2-(2-Hydroxy)ethoxy]ethylamino-1-(2,7-dichloro- --
Line 40 should read -- ppm (broad s, 3H, N — CH$_3$); 1.3-2.0 (broad s, 2H, NH, OH); --
Line 42 should read -- (br.d, 1 H, CH-O); 7.0-7.6 (m, 10 H). --
Line 44 should read -- "N-Desbutyl benflumetol"=2-n-butylamino-1-[2,7-dichloro- --
Line 53 should read -- $^1$H-NMR (200 Mhz, C$_6$D$_6$): 0.8 ppm (m, 3H, CH$_3$); 1.2 (m, --
Line 57, Title of Example 3 should read -- 2-n-Octylamino-1-[2,7-dichloro-9-(4-chlorobenzylidene)- --
Line 65 should read -- NH, OH); 2.5-2.7 (m, 3H, CH-N-CH$_2$); 2.95 (dd, 1 H, --

Column 15,
Line 2, Title of Example 4 should read -- 2-[2-(2-Hydroxy)ethoxy]ethylamino-1-[2,7-dichloro-9-(4- --
Line 8 should read -- OH-NH); 2.5-3.0 (m, 4H, CH$_2$-N-CH$_2$); 3.5 (m, 4H, --
Line 14 should read -- 9H-fluoren-4yl]ethanol (5c) --
Lines 23 and 24 should read -- (br., 2H, NH, OH); 2.5-2.7 (m, 3H, CH-N-CH$_2$); 3.0 (dd, 1 H, CH-N); 5.3 (dd,1 H, O-CH); 7.2-7.7 (m, 10H, --
Line 29 should read -- A mixture of 20 g 2,7-dichloro-9H-fluoren-4-oxiran, 17.7 --

Column 18,
Line 45, first line beneath Table 5 should read -- n=34; a=2.3498; b=0.7956; r=0.9814; x$^2$=3.6652 --

Column 19,
Line 35, first line beneath Table 6 should read -- n=34; a=3.3024; b=0.7216; r=0.9754; x$^2$=3.8764 --

UNITED STATES PATENT AND TRADEMARK OFFICE
CERTIFICATE OF CORRECTION

PATENT NO.    : 6,329,552 B2
DATED         : December 11, 2001
INVENTOR(S)   : Thomas Allmendinger et al.

It is certified that error appears in the above-identified patent and that said Letters Patent is hereby corrected as shown below:

<u>Column 21</u>,
Lines 24-25 should read -- A compound of claim 1 wherein R is $C_1$-$C_8$ alkyl, and X is 4-chlorophenyl, or a salt thereof. --
Lines 26-27 should read -- A compound of claim 3 wherein the $C_1$-$C_8$ alkyl is selected from methyl, n-butyl, sec-butyl, n-pentyl or n-octyl. --
Lines 28-29 should read -- The compound of claim 1 wherein R is n-butyl and X is 4-chlorophenyl, or a salt thereof. --

Signed and Sealed this

Fourteenth Day of May, 2002

*Attest:*

*Attesting Officer*

JAMES E. ROGAN
*Director of the United States Patent and Trademark Office*